US00PP30770P2

(12) United States Plant Patent
Winner

(10) Patent No.: US PP30,770 P2
(45) Date of Patent: Jul. 30, 2019

(54) ***COREOPSIS* PLANT NAMED 'GOLDEN STARDUST'**

(50) Latin Name: ***Coreopsis* hybrid**
Varietal Denomination: Golden Stardust

(71) Applicant: Ball Horticultural Company, West Chicago, IL (US)

(72) Inventor: Blair Winner, Ventura, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/999,988

(22) Filed: Sep. 6, 2018

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./263.1, 417
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Coreopsis* plant named 'Golden Stardust', characterized by its single-type, medium yellow-orange colored inflorescences having a burgundy-red colored eye zone, medium green-colored foliage, and moderately vigorous, upright growth habit, is disclosed.

1 Drawing Sheet

Latin name of genus and species of plant claimed: *Coreopsis* hybrid.

Variety denomination: 'Golden Stardust'.

BACKGROUND OF THE INVENTION

The present invention relates to a new and distinct cultivar of *Coreopsis* plant botanically known as *Coreopsis* hybrid and hereinafter referred to by the cultivar name 'Golden Stardust'.

The new cultivar originated in a controlled breeding program in Santa Paula, Calif. during October 2011. The objective of the breeding program was the development of *Coreopsis* cultivars having substantially continuous blooming throughout the summer, and upright growth habits.

The new *Coreopsis* cultivar is the result of open-pollination. The female (seed) parent of the new cultivar is the proprietary *Coreopsis* hybrid breeding selection coded 79571-21op, not patented, characterized by its dark yellow-colored flowers, light green-colored foliage, and moderately vigorous, upright growth habit. The male (pollen) parent of the new cultivar is unknown. The new cultivar was discovered and selected as a single flowering plant within the progeny of the above stated open-pollination during May 2012 in a controlled environment in Santa Paula, Calif.

Asexual reproduction of the new cultivar by terminal stem cuttings since May 2012 in Santa Paula, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Golden Stardust' as a new and distinct cultivar of *Coreopsis* plant:

1. Single-type, medium yellow-orange colored inflorescences having a burgundy-red colored eye zone;
2. Medium green-colored foliage; and
3. Moderately vigorous, upright growth habit.

Plants of the new cultivar differ from plants of the female parent primarily in having a different ray floret color and darker foliage color.

Of the many commercially available *Coreopsis* cultivars, the most similar in comparison to the new cultivar is the *Coreopsis* cultivar UpTick Yellow & Red 'Baluptowed', U.S. Plant Pat. No. 28,865. However, in comparison, plants of the new cultivar differ from plants of 'Baluptowed' in at least the following characteristics:

1. Plants of the new cultivar have fewer ray florets than plants of 'Baluptowed';
2. Plants of the new cultivar have smaller simple and trifoliate leaves than plants of 'Baluptowed'; and
3. Plants of the new cultivar have smaller diameter inflorescences than plants of 'Baluptowed'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Golden Stardust'. The plants were grown in one-gallon containers for approximately 4 weeks in a greenhouse in Elburn, Ill. followed by approximately 9 weeks in an outdoor nursery in West Chicago, Ill. Plants were given two pinches, one at one week before transplant and one two weeks after transplant.

DETAILED BOTANICAL DESCRIPTION

Figure 1:
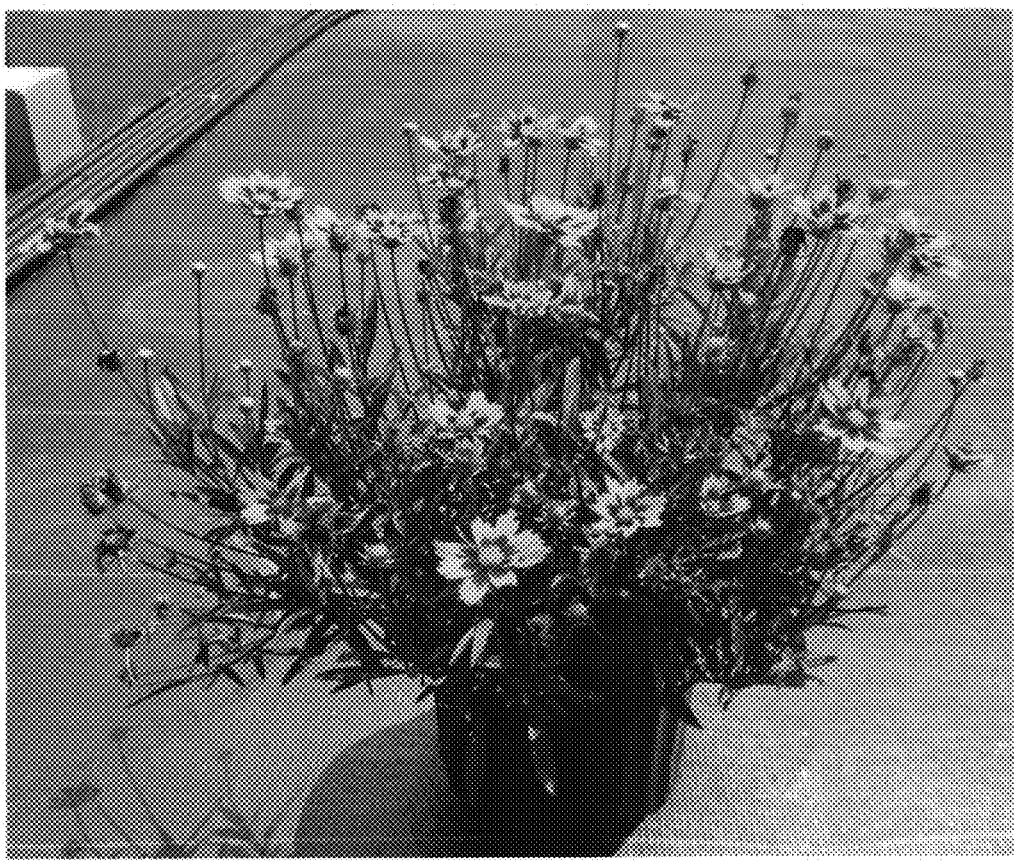
FIG. 1 illustrates a side view of the overall growth and flowering habit of 'Golden Stardust'.
Figure 2:
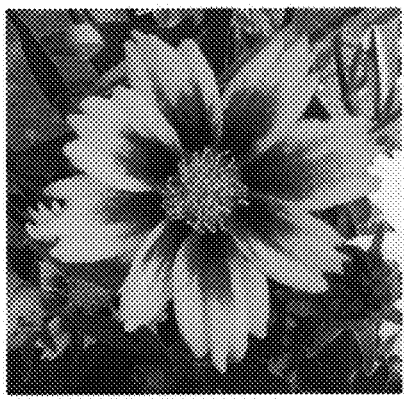
FIG. 2 illustrates a close-up view of an inflorescence of 'Golden Stardust'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2018 under natural light conditions in West Chicago, Ill.

The following descriptions and measurements describe approximately four-month old plants produced from cuttings from stock plants and grown under conditions comparable to those used in commercial practice. The plants were grown in one-gallon containers for approximately 4 weeks in a greenhouse in Elburn, Ill. followed by approximately 9 weeks in an outdoor nursery in West Chicago, Ill. Plants were given two pinches, one at one week before transplant and one two weeks after transplant. Greenhouse temperatures in Elburn, Ill. were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Coreopsis* hybrid 'Golden Stardust'.

Parentage:

*Female parent.*—Proprietary *Coreopsis* hybrid breeding selection coded 79571-21op, not patented.

*Male parent.*—Unknown.

Propagation:

*Type cutting.*—Terminal stem.

*Time to initiate roots.*—Approximately 10 to 12 days at 70° F. (21° C.).

*Time to produce a rooted cutting.*—Approximately 5 to 6 weeks at 70° F. (21° C.).

*Root description.*—Fibrous, thin, white to light brown in color.

*Rooting habit.*—Freely branching, dense.

Plant description:

*Commercial crop time.*—Approximately 10 to 12 weeks from a rooted cutting to finish in a one-gallon container.

*Growth habit and general appearance.*—Herbaceous perennial, moderately vigorous, upright growth habit.

*Hardiness.*—USDA zone 5a (−20° F. to −15° F./−28.9° C. to −26° C.).

*Size.*—Height from soil level to top of plant plane: Approximately 37.0 cm. Width: Approximately 40.0 cm.

*Branching habit.*—Freely branching, pinching improves basal branching. Quantity of lateral branches per plant: 3 main branches each having approximately 6 to 8 lateral branches.

*Lateral branches.*—Strength: Moderately strong. Length to base of peduncle: Approximately 21.0 cm. Diameter: Approximately 3.0 mm to 5.0 mm. Length of central internode: Approximately 3.5 cm. Texture: Moderately pubescent. Color of young and mature stems: 146A to 146B.

Foliage description:

*General description.*—Quantity of leaves per main branch: Approximately 8. Type: Simple and trifoliate. Fragrance: None detected. Arrangement: Opposite. Aspect: Acute angle to stem. Shape of leaf and leaflet: Narrowly elliptic. Margin of leaf and leaflet: Entire, ciliate. Apex of leaf and leaflet: Acute. Base of leaf and leaflet: Attenuate, simple leaf sessile. Venation pattern: Pinnate.

*Simple leaf.*—Length: Approximately 6.0 cm. Width: Approximately 1.0 cm. Texture of upper surface: Sparsely pubescent. Texture of lower surface: Moderately pubescent. Color of upper surface of young and mature foliage: 137A with indistinguishable venation. Color of lower surface of young and mature foliage: Closest to 146A with indistinguishable venation.

*Mature trifoliate leaf.*—Length of mature trifoliate leaf: Approximately 6.5 cm. Width of mature trifoliate leaf: Approximately 3.5 cm. Length of terminal leaflet: Approximately 5.0 cm. Width of terminal leaflet: Approximately 1.0 cm. Length of lateral leaflet: Approximately 1.8 cm. Width of lateral leaflet: Approximately 4.0 mm. Texture of upper surface: Sparsely pubescent. Texture of lower surface: Moderately pubescent. Color of upper surface of young and mature foliage: 137A with indistinguishable venation. Color of lower surface of young and mature foliage: Closest to 146A with indistinguishable venation. Length of petiole of mature trifoliate leaf: Approximately 1.2 cm. Diameter of petiole of mature trifoliate leaf: Approximately 3.0 mm. Texture of petiole of mature trifoliate leaf: Sparsely pubescent. Color of upper and lower surfaces of petiole of mature trifoliate leaf: 146B.

Flowering description:

*Flowering habit.*—'Golden Stardust' is freely flowering under outdoor growing conditions with substantially continuous blooming from spring through late autumn.

*Lastingness of individual inflorescence on the plant.*—Approximately 7 to 10 days.

Inflorescence description:

*General description.*—Type: Daisy-type composite, actinomorphic. Persistent, but doesn't require cleaning to flower. Shape: Round. Aspect: Primarily erect. Arrangement: Terminal capitulum, positioned above the foliage. Quantity per plant: Approximately 27. Diameter: Approximately 4.6 cm. Depth: Approximately 1.5 cm. Fragrance: Slightly acrid.

*Peduncle.*—Strength: Strong, flexible. Aspect: Erect. Length: Approximately 9.5 cm to 12.5 cm. Diameter: Approximately 2.0 mm. Texture: Sparsely pubescent. Color: 146A.

*Bud.*—Rate of opening: Generally takes 4 to 5 days for bud to progress from first color to fully open inflorescence. Quantity per plant: Approximately 25.

*Bud just before opening.*—Shape: Obovoid. Width: Approximately 9.0 mm. Depth: Approximately 8.0 mm. Color: 163A.

*Ray florets.*—Quantity per inflorescence: Approximately 8 to 9. Arrangement: In a single whorl, slightly imbricate. Aspect: Flattened. Shape: Oblong to obovate. Margin: Entire. Apex: Incised. Base: Rounded. Length: Approximately 2.3 cm. Width: Approximately 1.0 cm to 1.1 cm. Texture of upper and lower surfaces: Glabrous, longitudinal ribs. Color of upper surface when first and fully open:

14A with base of 187A to 187B. Color of lower surface when first open: 14B with a faint underlay of 187B at base.

*Disc florets.*—Quantity per inflorescence: Approximately 115. Arrangement: Massed in center of inflorescence. Shape: Tubular. Margin: Entire. Apex: Five acute tips. Base: Fused. Length: Approximately 7.0 mm. Diameter at tube opening: Approximately 2.0 mm. Diameter at base: Approximately 1.0 mm. Texture of outer surface: Glabrous. Texture of inner surface: Glabrous with glandular pubescence on tips. Color of upper or inner surface when first and fully open: Closest to 17C, translucent; tips of 17B. Color of lower or outer surface when fully open: Closest to 17C, translucent; tips of 17B, base of 145D.

*Disc.*—Diameter: Approximately 1.0 cm. Depth: Approximately 5.0 mm.

*Receptacle.*—Shape: Dome. Height: Approximately 2.0 mm. Diameter at base: Approximately 5.0 mm. Color: 145D.

*Phyllaries.*—Quantity per inflorescence Approximately 16. Arrangement: In two equally divided whorls. Base of inner whorl fused into cup-shaped base surrounding receptacle, imbricate, held close to ray florets.

*Outer phyllaries.*—Shape: Lanceolate. Margin: Entire, ciliate. Apex: Acute. Base: Truncate. Length: Approximately 8.0 mm. Width: Approximately 2.0 mm. Texture of upper and lower surfaces: Glabrous, glossy. Color of upper and lower surfaces: 137A with colorless margins.

*Inner phyllaries.*—Shape of free portion: Ovate. Margin: Entire. Apex: Acute. Base: Fused. Length: Approximately 1.2 cm. Width: Approximately 6.0 mm. Texture of upper and lower surfaces: Glabrous. Color of upper and lower surfaces: 163C with cup-shaped portion of closest to 146C.

*Reproductive organs.*—Androecium: Present on disc florets only. Stamen quantity: 5. Stamen length: Approximately 5.0 mm. Filament length: Approximately 2.5 mm. Filament color: 154D. Anther shape: Oblong, basifixed. Anther length: Approximately 2.5 mm. Anther color: 17B. Pollen amount: Abundant. Pollen color: 17A. Gynoecium: Present on disc florets only. Pistil quantity: 1 per floret. Pistil length: Approximately 7.0 mm. Stigma shape: 2-branched. Stigma length: Each branch approximately 1.0 mm. Stigma color: 17B. Style length: Approximately 5.0 mm. Style color: 154D. Ovary length: Approximately 2.0 mm. Ovary color: 145D.

Seed and fruit production: Neither seed nor fruit production has been observed.

Disease and pest resistance: Resistance to pathogens and pests common to *Coreopsis* has not been observed.

What is claimed is:

1. A new and distinct cultivar of *Coreopsis* plant named 'Golden Stardust', substantially as herein illustrated and described.

* * * * *